United States Patent
Hillmann et al.

(10) Patent No.: US 10,743,766 B2
(45) Date of Patent: Aug. 18, 2020

(54) METHOD FOR FILTERING REFLEXES IN FULL-FIELD SETUPS FOR OPHTHALMOLOGIC IMAGING BY SEPARATED ILLUMINATION AND DETECTION APERTURES

(71) Applicant: THORLABS GMBH

(72) Inventors: Dierck Hillmann, Lübeck (DE); Gereon Hüttmann, Lübeck (DE); Gesa Lilith Franke, Hamburg (DE); Helge Sudkamp, Lübeck (DE); Laura Hinkel, Lübeck (DE); Peter Koch, Lübeck (DE); Jörn Wollenzin, Lübeck (DE)

(73) Assignee: THORLABS GMBH, Dachau (DE)

( * ) Notice: Subject to any disclaimer, the term of this patent is extended or adjusted under 35 U.S.C. 154(b) by 77 days.

(21) Appl. No.: 16/115,975

(22) Filed: Aug. 29, 2018

(65) Prior Publication Data
US 2018/0368680 A1    Dec. 27, 2018

Related U.S. Application Data

(63) Continuation of application No. 14/610,319, filed on Jan. 30, 2015, now Pat. No. 10,070,788.

(60) Provisional application No. 61/934,265, filed on Jan. 31, 2014.

(51) Int. Cl.
| | | |
|---|---|---|
| A61B 3/15 | (2006.01) | |
| A61B 3/10 | (2006.01) | |
| A61B 3/12 | (2006.01) | |
| G02B 27/10 | (2006.01) | |

(Continued)

(52) U.S. Cl.
CPC .............. *A61B 3/156* (2013.01); *A61B 3/102* (2013.01); *A61B 3/12* (2013.01); *A61B 3/1225* (2013.01); *G02B 27/108* (2013.01); *G02B 27/144* (2013.01); *G02B 3/0087* (2013.01)

(58) Field of Classification Search
CPC .. A61B 3/00; A61B 3/102; A61B 3/12; A61B 3/1225; A61B 3/15; A61B 3/156; A61B 3/158; A61B 3/18
USPC .............. 250/227.14–227.2, 227.23–227.27; 351/200–247
See application file for complete search history.

(56) References Cited

U.S. PATENT DOCUMENTS

| | | |
|---|---|---|
| 3,925,793 A | 12/1975 | Matsumura et al. |
| 4,421,391 A * | 12/1983 | Matsumura ............ A61B 3/103 351/211 |
| 4,422,736 A | 12/1983 | Nunokawa |

(Continued)

OTHER PUBLICATIONS

Mujat, M., Iftimia, N.V., Ferguson, R.D., Hammer, D.X. Swept-source parallel OCT. Proc. SPIE 7168, Optical Coherence Tomography and Coherence Domain Optical Methods in Biomedicine XIII. Feb. 2009, p. 71681E.

(Continued)

*Primary Examiner* — William R Alexander
*Assistant Examiner* — Ephrem Z Mebrahtu
(74) *Attorney, Agent, or Firm* — Myers Wolin, LLC

(57) ABSTRACT

A parallel detecting optical coherence tomography (OCT) setup and method, in which the light paths of the illumination of the sample and of the detection of the backscattered light do not use the same apertures. The separation of illumination and detection apertures filters these disturbing reflexes from the backscattered light of the sample and significantly increases image quality.

10 Claims, 3 Drawing Sheets

(51) Int. Cl.
*G02B 27/14* (2006.01)
*G02B 3/00* (2006.01)

(56) References Cited

U.S. PATENT DOCUMENTS

| | | | |
|---|---|---|---|
| 5,543,865 A | 8/1996 | Nanjo | |
| 6,072,623 A | 6/2000 | Kitajima et al. | |
| 2002/0101567 A1* | 8/2002 | Sumiya | A61B 3/1176 351/206 |
| 2003/0025917 A1 | 2/2003 | Suhami | |
| 2006/0055936 A1 | 3/2006 | Yun et al. | |
| 2008/0181477 A1 | 7/2008 | Izatt et al. | |
| 2008/0291463 A1* | 11/2008 | Milner | A61B 1/00096 356/491 |
| 2009/0201467 A1 | 8/2009 | Smith et al. | |
| 2010/0149543 A1* | 6/2010 | Nebosis | G01N 21/4795 356/450 |
| 2010/0182612 A1 | 7/2010 | Yoshida et al. | |
| 2011/0202044 A1 | 8/2011 | Goldschleger et al. | |
| 2011/0306875 A1* | 12/2011 | Fischer | G01B 9/02044 600/425 |
| 2014/0111772 A1 | 4/2014 | Ikegami | |
| 2014/0176903 A1 | 6/2014 | Qiu et al. | |
| 2015/0015845 A1 | 1/2015 | Spaide et al. | |
| 2015/0131050 A1 | 5/2015 | Bublitz et al. | |

OTHER PUBLICATIONS

Bonin, T., Franke, G.L., Hagen-Eggert, M., Koch, P., Hüttmann, G. In vivo Fourier-domain full-field OCT of the human retina with 1.5 million A-lines/s. Optics Letters, vol. 35, Issue 20. 2010, pp. 3432-3434.

Hillmann, D., Lührs, Chr., Bonin, T., Koch, P., Hüttmann, G. Holoscopy—holographic optical coherence tomography. Optics Letters, vol. 36, Issue 13. 2011, 2390-2.

Hillmann, D., Franke, G., Lührs, C., Koch, P., Hüttmann, G. Efficient holoscopy image reconstruction. Optics Express, vol. 20, Issue 19, pp. 21247-21263. 2012.

Hillmann, D., Franke, G., Hinkel, L., Bonin, T., Koch, P., Hoffmann, G. Off-axis full-field swept-source optical coherence tomography using holographic refocusing. Proc. SPIE 8571, Optical Coherence Tomography and Coherence Domain Optical Methods in Biomedicine XVII. 2013, 857104.

El-Bayadi, G. New method of slit-lamp micro-ophthalmoscopy. Brit. J. Ophthal., vol. 37, pp. 625628. 1953.

* cited by examiner

METHOD FOR FILTERING REFLEXES IN FULL-FIELD SETUPS FOR OPHTHALMOLOGIC IMAGING BY SEPARATED ILLUMINATION AND DETECTION APERTURES

CROSS-REFERENCE TO RELATED APPLICATIONS

This application is a continuation of U.S. patent application Ser. No. 14/610,319 filed on Jan. 30, 2015, which claims the benefit of U.S. Provisional Patent Application No. 61/934,265 filed on Jan. 31, 2014. The disclosures of U.S. patent application Ser. No. 14/610,319 and U.S. Provisional Patent Application No. 61/934,265 are hereby incorporated by reference.

FIELD OF THE INVENTION

The present invention relates to the field of ophthalmologic imaging, and more particularly to systems and methods for filtering reflexes in full-field setups for ophthalmologic imaging by separated illumination and detection apertures.

BACKGROUND

In ophthalmology tomographic imaging of scattering structures of the eye is of high interest. The standard technique is optical coherence tomography (OCT), employing an interferometric setup and a spatially coherent light source with a short temporal coherence length. Conventional OCT systems acquire volumetric data by scanning a focused beam over the sample and consequently, measurement speed is limited by the scanning speed. To further increase imaging speed methods with parallel detection of scattered light have been developed. Since in those tomographic ophthalmic imaging techniques that employ parallel detection no confocal imaging is used, disturbing reflexes reduce the image quality significantly.

Below are some existing ophthalmology tomographic imaging techniques:

In Fourier-Domain optical coherence tomography (FD-OCT) an interference signal over a broad spectral width is recorded in an interferometric setup. This is achieved by either detecting the signal of a broadband light source spectrally resolved (Spectral-Domain OCT) or by recording an interference signal over time, while a laser source is spectrally tuned (Swept-Source OCT). Considering the entire spectral range, the short temporal coherence length of the light source allows for an optical path length measurement of backscattered and/or reflected light from a sample in one of the interferometer arms. The path length is encoded in the interference signal, which is generated by superimposing light from sample and reference arm. Measurements of interference signals at several wavelengths allow a depth encoded profile of the sample (A-scan). The main area of application for OCT is ophthalmologic imaging, especially tomographic images of the retina (posterior eye segment) and structures in the anterior eye segment (cornea, ocular lens, iridocorneal angle).

Swept-Source OCT (SS-OCT) uses a setup with a tunable light source. While tuning the light source a wavelength-dependent interference spectrum is measured. The tuning range of the laser, which corresponds to its entire spectrum, defines the coherence length of the system. The coherence length of a single wavelength is defined by the instantaneous line width. A tomographic data volume is measured conventionally by sequential data acquisition at different points, i.e., lateral scanning of the sample. Generally the sample is screened by two lateral scanners and the backscattered light is detected with a point detector. Measurement speed for sequential data acquisition might be limited by the speed of the scanners in this scenario. A phase stable detection over the whole volume is not possible in most cases. Scanning fiber based OCT systems have a confocal gating, i.e. only sample structures in the focus are illuminated and detected, while out-of-focus photons are rejected. Therefore multiple scattered photons occurring in strongly scattering media are suppressed.

A setup with a partly parallelized data acquisition is called Line-Field-OCT or Swept-Source parallel OCT (see reference 1). The backscattered light from the sample is detected in parallel in one lateral dimension, while it is scanned in the other lateral direction. The detector consists of multiple individual elements, which are arranged in a line, e.g., a line scan camera. Measurement speed is generally improved by the partial parallelization. Multiple scattered photons are not suppressed, if their last scattering event is recorded by the detector.

For a completely parallel detection in two dimensions the sample is illuminated homogeneously and spatially coherent (Full-Field Swept-Source OCT, short: FF-SS-OCT). An area scan camera is used as detector. In FF-SS-OCT the sample or rather a part of the sample is imaged onto the area camera. An advantage of this method is the increased measurement speed. While in scanning OCT systems the scanners or the tuning speed limit the measurement speed, in FF-SS-OCT the frame rate of the camera is in general the most limiting factor. All parallel detected A-scans are phase stable to each other. With this method scattered photons from all depths are detected, which are filtered in scanning systems by the confocal gating. Thus the measurement depth is larger in comparison to scanning systems, but the lateral resolution degrades out-of-focus. This degradation limits the useful measurement depth, especially at high lateral resolution. Another disadvantage of FF-SS-OCT is the detection of multiple scattered photons due to the parallel detection. Ophthalmic imaging with FF-SS-OCT has been demonstrated successfully, showing in vivo retina measurements (see reference 2)

Holoscopy is method related to FF-SS-OCT where the sample is not necessarily imaged onto the camera, but wave fields of the backscattered light from the sample are detected (see references 3 and 4). The focusing in all depth is performed in the following reconstructions. This has the advantage, that the lateral resolution does not degrade out-of-focus, but is constant over the whole volume. The reconstruction algorithm for holoscopy is also suitable for increasing the focus depth in FF-SS-OCT data.

By implementing an off-axis reference illumination in FF-SS-OCT or holoscopy it is possible to separate the signal of the interference of the sample with the reference light from its complex-conjugated signal as well as from DC and autocorrelation signals and to suppress the non-relevant signal terms. This increases the sensitivity of the imaging and avoids an overlay of multiple signal parts. (See reference 5).

All OCT techniques and related imaging methods mentioned so far are in particular suitable for scattering samples. If a sample has highly reflecting and weakly scattering parts, the strong reflections induce overexposure artifacts in the images and decrease the sensitivity of the measurements.

More significantly, strong reflexes that are not within the measurement range, induce an incoherent background noise on all depth profiles/A-scans.

In other ophthalmologic imaging modalities, which have spatial incoherent illumination, strong reflexes induce image artifacts as well. This is the case for fundus cameras, where photographs of the posterior eye segment are taken, as well as for slit lamps, where all segments of the eye can be visualized enabling a variable slit shaped illumination. The artifacts caused by strong reflexes mainly lead to an overexposure of the detector, or the reflexes overshadow the actual image of the retina. The approaches to reduce those artifacts are based on the separation of illumination and detection apertures.

In conventional fundus camera setups a ring shaped aperture in the illumination light path is imaged into the plane of the pupil (References 6, 7, 8). The ring shaped illumination generates only reflexes in the outer areas, which are reflected at an angle, in a way, that they are not imaged onto the detector. The retina is illuminated divergently. The backscattered light is refracted via the optical elements of the eye and projected onto the detector. Such an aperture is not possible with coherent light, as the light will interfere on the retina and not create a constant illumination.

In conventional slit lamp setups the eye is illuminated at an angle. The angle is adjusted in a way that the backscattered light is detected, while the reflected light does not reach the detection light path (references 9, 10). When using a coherent light source the illumination of the retina is not uniform due to interference effects.

Both fundus cameras and slit lamps use conventional light sources, e.g., filament lamps or halogen bulbs. Those light sources are both spatially and temporally incoherent. Therefore there are no additional interference effects, which prevent a uniform illumination of the sample. In addition, these techniques do not provide depth information for scattering tissue.

So far there is no imaging modality that provides volumetric sample information with a parallel detection and spatially coherent light that implements reflex reduction methods to increase SNR by decreasing stray light.

As described above, existing techniques have drawbacks and disadvantages. Therefore, there is a need for an imaging system and method that allows imaging a larger portion of the eye than possible with any of today's optical imaging systems. Anterior and posterior segment can be imaged in parallel. Using parallel detection, volumetric imaging equivalent to >5 million A-scans per second (comparing to scanned OCT technology) are possible and provide very fast acquisition. The parallel detection scheme has a much higher efficiency, as it misses the confocal gating that is used in the prior art of eye inspection using optical coherence tomography. Hence a larger imaging speed can be applied within the restrictions of eye safety regulations.

SUMMARY

The present invention provides a parallel detecting OCT setup and method where the light paths of the illumination of the sample and of the detection of the backscattered light do not use the same apertures. The separation of illumination and detection apertures filters these disturbing reflexes from the backscattered light of the sample and significantly increases image quality. Similar approaches have been implemented in non-tomographic ophthalmologic imaging modalities with spatially incoherent light sources (mainly fundus cameras, slit lamps). However, different technical constraints apply and special technical arrangement have to be used for tomographic imaging. For example, the light sources that are used in fundus imaging are white light sources (such as a halogen lamp) which are incoherent. For tomographic imaging, spatially (and temporally) coherent radiation (a swept source laser) is required to obtain the depth information. Using the previous approaches (such as ring illumination) to separate the illumination from the detection aperture results in disturbing interference patterns on the retina if coherent radiation is used, whereas everything is fine with incoherent light. This poses a problem when using the ring aperture for tomographic imaging, as the areas with destructive interference cannot be imaged. Therefore, the approaches provided by the present invention have a unique advantage that it does not cause interference signals on the retina.

One embodiment of the present invention provides an ophthalmologic imaging system including: a tunable light source; a first optical system to focus light from the light source onto a mirror, such that the mirror reflects the light onto a sample in a first light path; a second optical system configured to direct scattered light from the sample onto a detector in a second light path, and the second optical system is further configured to direct a reference beam onto the detector, the reference beam being either on-axis or off-axis to the second path; wherein the mirror is configured to reflect the light in the first light path, which is an angle to the second light path.

Another embodiment of the present invention provides an ophthalmologic imaging system including: a tunable light source; a mirror with a hole; a first optical system to focus light from the light source into the hole of the mirror, such that the light passes through the hole is focused onto the cornea by a lens and illuminates the retina divergently; a second optical system configured to direct scattered light from the sample that is reflected by the mirror onto a detector, and the second optical system is further configured to direct a reference beam onto the detector, the reference beam being either on-axis or off-axis to the second path.

Another embodiment of the present invention provides an ophthalmologic imaging system including: a tunable light source; a mirror with a hole; a gradient-index (GRIN) lens placed in the hole; a first optical system to direct light from the light source onto the GRIN lens, such that the light passes through the GRIN lens is focused onto the cornea by a lens and illuminates the retina divergently; a second optical system configured to direct scattered light from the sample that is reflected by the mirror onto a detector, and the second optical system is further configured to direct a reference beam onto the detector, the reference beam being either on-axis or off-axis to the second path.

DETAILED DESCRIPTION OF THE PREFERRED EMBODIMENTS

Figure 1:
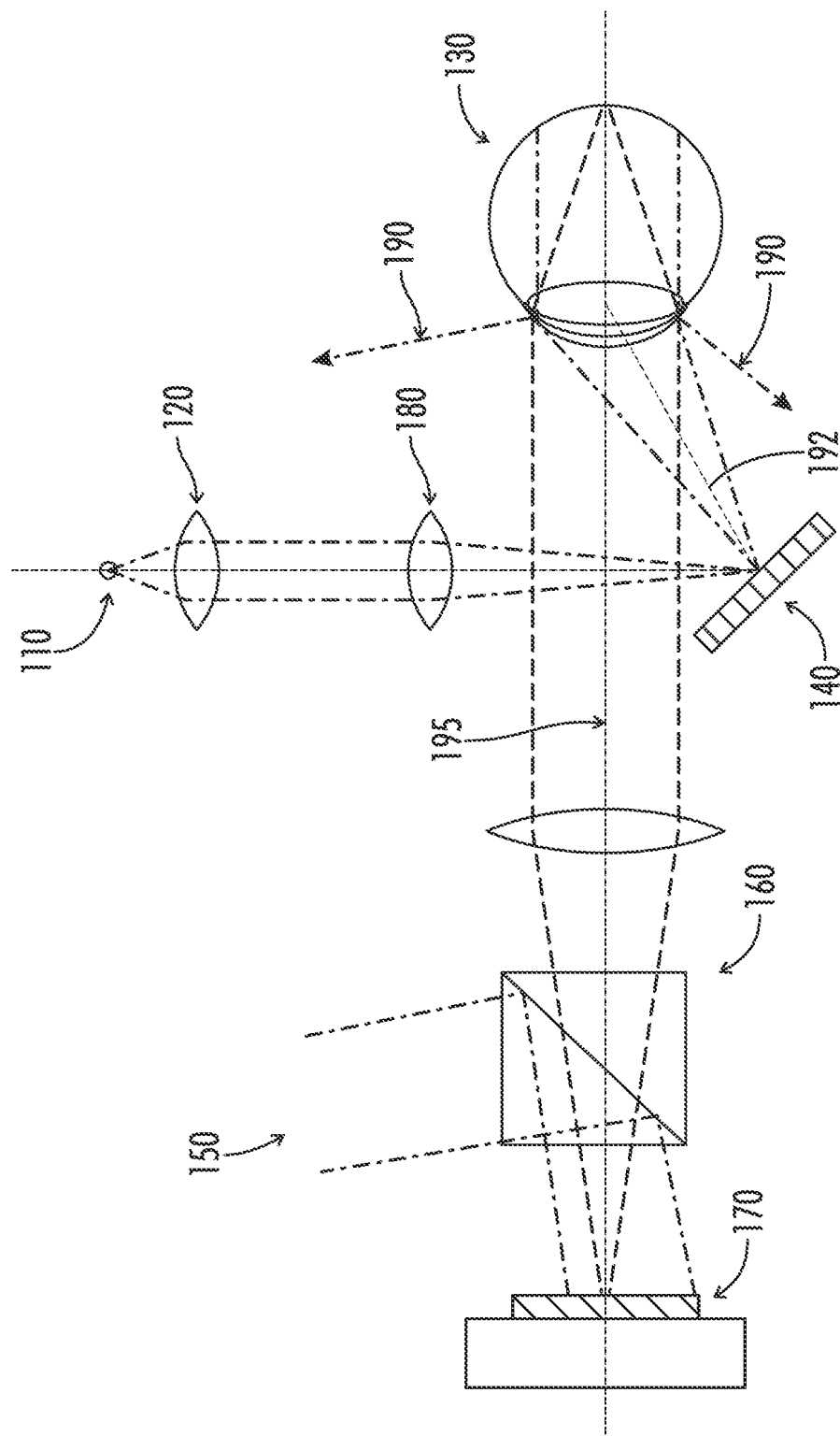
FIG. 1 is a ophthalmologic imaging setup in accordance with an embodiment of the invention.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

This disclosure describes the best mode or modes of practicing the invention as presently contemplated. This description is not intended to be understood in a limiting sense, but provides an example of the invention presented solely for illustrative purposes by reference to the accompanying drawings to advise one of ordinary skill in the art of the advantages and construction of the invention. In the various views of the drawings, like reference characters designate like or similar parts.

Ophthalmologic imaging is sensitive to image artifacts that are caused by reflections from the eye itself. Especially the front side of the cornea is strongly reflecting. In swept-source OCT and related tomographic imaging methods these reflections cause a reduced sensitivity due to overexposure, coherent background, and/or incoherent background noise. By implementing separated apertures for the illumination of the eye and the detection of the backscattered light strong reflections at interfaces like the cornea can be filtered before detection. In one embodiment of the invention, an interferometric setup for ophthalmic imaging includes one or more of the following components:

- A tunable light source; preferably, the total coherence length, defined by the spectral width of the tuning range, does not exceed 50 µm. The instantaneous coherence length, defined by the instantaneous line width of the spectral range during one shot, preferably, is at least 200 µm.
- A detector consisting of several pixels, preferably, recording data with an acquisition speed of at least 500 images per second.
- A reference illumination with an incident direction that can differ from the incident direction of the sample light on the detector (off axis).
- A spatial coherent or partly coherent illumination of the eye.
- A separated illumination and detection aperture for the suppression of reflected light from plane or curved interface, preferably, of at least 10 dB.

Separated illumination and detection apertures in an interferometric setup could be implemented as follows:

In one embodiment of the invention, the angle under which the sample is illuminated differs from the detection angle of the backscattered light, as illustrated by FIG. 1. A light source 110 is used to illuminate the sample 130. The illumination light from light source 110 is focused by a collimator 120 and a lens 180 onto a mirror 140. The mirror reflects the illumination light into the sample 130. The backscattered light from the sample 130 is detected by a camera 170. A reference signal 150 (which can be either on-axis or off-axis) is directed onto the camera 170 via a beam splitter 160. As shown in FIG. 1, the illumination light path is reflected by the mirror 140, which is placed at an angle to the detection light path. The angle of the mirror is adjusted in a way that the desired area of the sample 130 is illuminated and the backscattered light detected while the reflexes of the cornea are not in the detection beam path.

Figure 2:
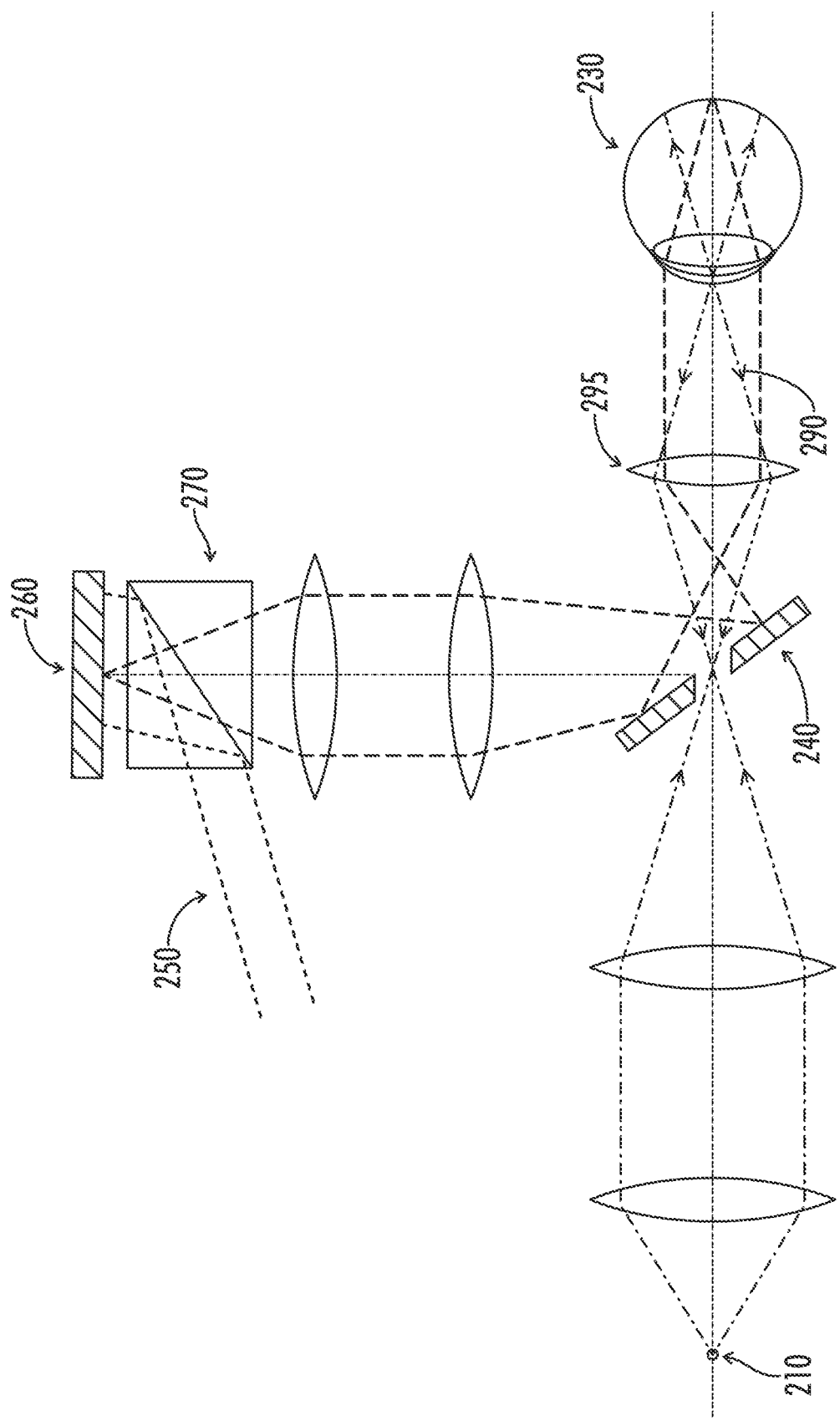
FIG. 2 is a ophthalmologic imaging setup in accordance with another embodiment of the invention.

In another embodiment of the invention, central reflexes of the cornea can be filtered by creating a focus on the cornea or slightly beneath the cornea surface. The illumination of the retina is divergent. Backscattered light from the retina is detected while reflected light from the cornea is filtered, as shown in FIG. 2. A light source 210 is used to illuminate the eye 230. A collimator 220 and a lens (280) focus the illumination light path through a central hole in an angled mirror 240. Further optical elements create a focus on the cornea, while the retina is divergently illuminated. The backscattered light is converted into the far field by the optics of the eye. The central cornea reflex does not reach the detection camera, since it is imaged back through the hole in the mirror and/or is absorbed by a non-reflecting area around the hole, while most of the light from the retina is deflected by the mirror 240 onto the detector 260. Only a small part of the sample light is filtered by the mirror. A reference signal 250 (which can be either on-axis or off-axis) is directed onto the camera 260 via a beam splitter 270.

Figure 3:
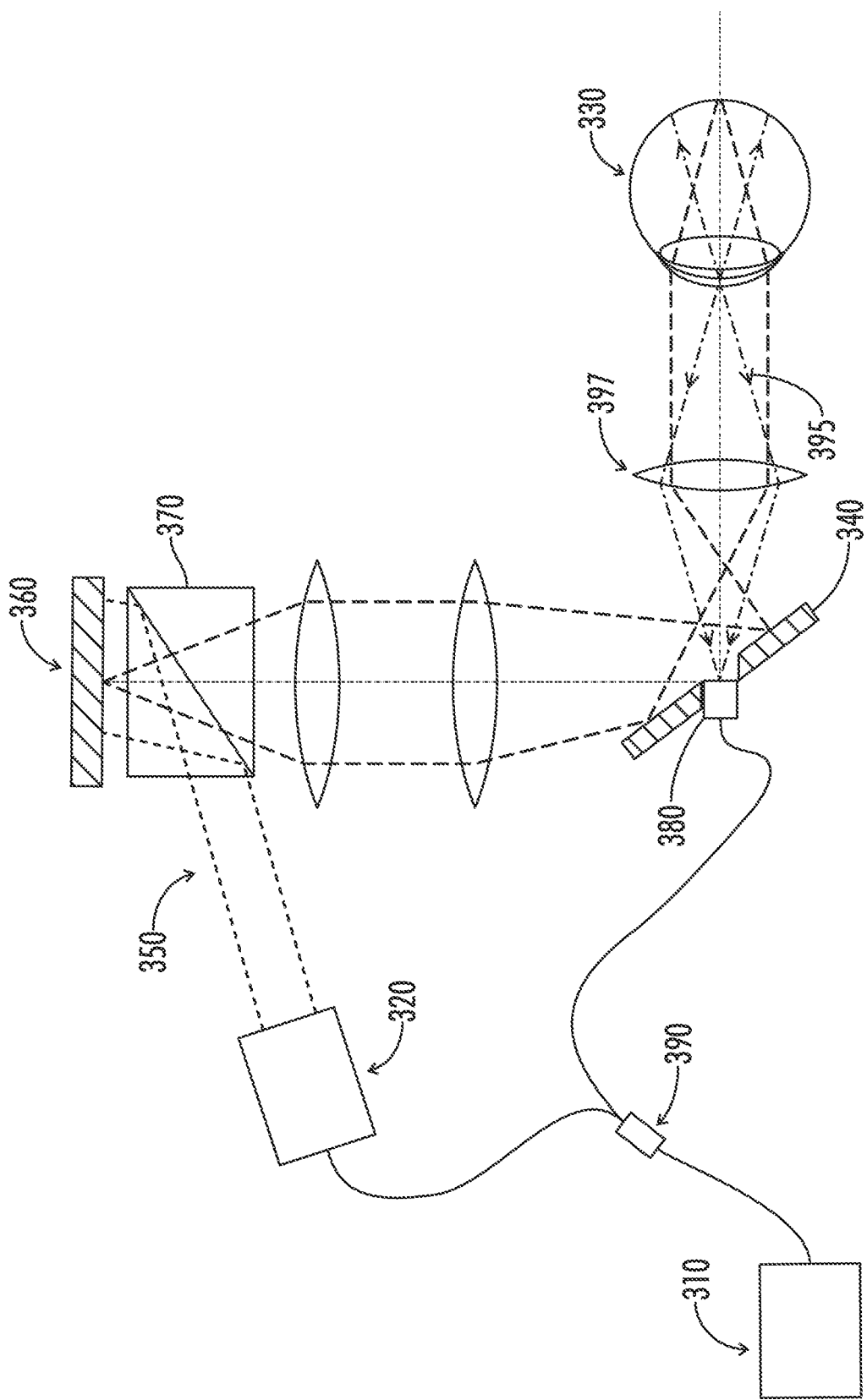
FIG. 3 a ophthalmologic imaging setup in accordance with yet another embodiment of the invention.

Another option to create a focus on the cornea is to position a Gradient-index (GRIN) lens with a suitable pitch length in a hole in an angled mirror, in accordance with one embodiment of the invention. FIG. 3 shows a GRIN lens 380 in a hole of the mirror 340. The illumination beam is converging when leaving the GRIN lens 380 and focused by an additional lens onto the cornea or slightly beneath the cornea surface of the eye 330. The backscattered light is converted into the far field by the optics of the eye. The central cornea reflex does not reach the detection camera, since it is imaged back through the hole in the mirror and/or is absorbed by a non-reflecting area around the hole, while most of the light from the retina is deflected by the mirror 340 onto the detector 360. Only a small part of the sample light is filtered by the mirror. An off-axis reference signal 350 is directed onto the camera 360 via a beam splitter 370. FIG. 3 also shows an arrangement according to an embodiment in which a light source 310 supplies both the illumination beam and reference beam. A coupler 390 that splits the light from light source 310 into two paths, one to the GRIN lens 380, another one to a collimator 320, which directs the reference beam 350 to a beam splitter 370. The beam splitter 370 directs the reference beam onto the detector 360. It is contemplated that other optical components and combinations thereof, such as lens, prisms, mirrors, fibers, etc., may be used to direct the light from the light source to the illumination path and the reference beam path. Note that although not shown in FIGS. 1 and 2, similar arrangements are contemplated to provide both the illumination beam and reference beam.

The backscattered light from the sample is collected by the detector—either via imaging the scattering volumetric sample or via the detection of wave fields from scatterers from all depths within the sample. In both cases the reconstruction algorithm developed for holoscopy can be used for data reconstruction.

REFERENCES

1. Mujat, M., Iftimia, N. V., Ferguson, R. D., Hammer, D. X. Swept-source parallel OCT. Proc. SPIE 7168, Optical Coherence Tomography and Coherence Domain Optical Methods in Biomedicine XIII. February 2009, p. 71681E.
2. Bonin, T., Franke, G. L., Hagen-Eggert, M., Koch, P., Hüttmann, G. In vivo Fourier-domain full-field OCT of the human retina with 1.5 million A-lines/s. Optics Letters, Vol. 35, Issue 20. 2010, pp. 3432-3434.
3. Hillmann, D., Lührs, Chr., Bonin, T., Koch, P., Hüttmann, G. Holoscopy—holographic optical coherence tomography. Optics Letters, Vol. 36, Issue 13. 2011, 2390-2.
4. Hillmann, D., Franke, G., Lührs, C., Koch, P Hüttmann, G. Efficient holoscopy image reconstruction. Optics Express, Vol. 20, Issue 19, pp. 21247-21263. 2012.
5. Hillmann, D., Franke, G., Hinkel, L., Bonin, T., Koch, P., Hüttmann, G. Off-axis full-field swept-source optical coherence tomography using holographic refocusing. Proc. SPIE 8571, Optical Coherence Tomography and Coherence Domain Optical Methods in Biomedicine XVII. 2013, 857104.
6. Nanjo, T. Fundus camera with partially common coaxial observation and photographing optical systems. United States Patents, 1996. U.S. Pat. No. 5,543,865.
7. Nunokawa, K. Eye fundus camera having ring slit mask in illumination system. United States Patent, 1981. U.S. Pat. No. 4,422,736.
8. Matsumura, I., Kohayakawa, Y. Eye fundus camera with focus setting device. United States Patent, 1974. U.S. Pat. No. 3,925,793.
9. El-Bayadi, G. New method of slit-lamp micro-ophthalmoscopy. Brit. J. Ophthal., Vol. 37, pp 625628. 1953.
10. Kitajima, N., Okamura, K. Slit lamp microscope. United States Patents, 2000. U.S. Pat. No. 6,072,623.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention. Furthermore, the foregoing describes the invention in terms of embodiments foreseen by the inventor for which an enabling description was available, notwithstanding that insubstantial modifications of the invention, not presently foreseen, may nonetheless represent equivalents thereto.

What is claimed is:

1. An ophthalmologic imaging system comprising:
a tunable light source configured to provide an illumination beam and a reference beam;
a mirror; and
an optical system configured to:
focus the illumination beam from the light source onto the mirror, such that the mirror reflects the light onto a sample in a first light path, and the light is partly scattered at a desired area of the sample and partly reflected at a plane or curved interface in the sample;
detect scattered light from the desired area of the sample by a detector situated in a second light path, and
direct the reference beam onto the detector, the reference beam being off-axis to the second path;
wherein an angle of the mirror is configured to reflect the light in the first light path, which is at an angle to the second light path; and
wherein the mirror is not in the second light path;
wherein the tunable light source has a total coherence length, defined by the spectral width of the tuning range, not exceeding 50 µm, and an instantaneous coherence length, defined by the instantaneous line width of the spectral range during the scan, of at least 200 µm;
wherein the detector is configured to collect the reflected light from the sample via imaging the scattering volumetric sample or via the detection of wave fields from scatterers from all depths within the sample.

2. The system of claim 1, wherein the detector has an acquisition speed of at least 500 images per second.

3. An ophthalmologic imaging system comprising:
a tunable light source configured to provide an illumination beam and a reference beam;
a mirror with a hole; and
an optical system configured to:
focus the illumination beam from the light source into the hole of the mirror, such that the illumination beam passes through the hole and illuminates a desired area in a sample through a lens, and the light is partly scattered at the desired area in the sample and partly reflected at a plane or curved interface in the sample, wherein the scattered light from the desired area in the sample is converted into far field light by a lens in the sample and the reflected light from the plane or curved interface in the sample is imaged back through the hole by the lens;
direct the far field light onto a detector by the mirror; and
direct the reference beam onto the detector, the reference beam being off-axis to a light path from the sample to the detector;
wherein the tunable light source has a total coherence length, defined by the spectral width of the tuning range, not exceeding 50 µm, and an instantaneous coherence length, defined by the instantaneous line width of the spectral range during the scan, of at least 200 µm;
wherein the detector is configured to collect the reflected light from the sample via imaging the scattering volumetric sample or via the detection of wave fields from scatterers from all depths within the sample.

4. The system of claim 3, wherein the detector has an acquisition speed of at least 500 images per second.

5. The system of claim 3, wherein the sample is an eye and the desired area is on the retina of the eye, such that a focus is on or slightly beneath the cornea and the cornea reflex passes through the hole in the mirror, not reaching the detector.

6. An ophthalmologic imaging method comprising:
illuminating a sample by a beam from a tunable light source;
focusing the beam onto a mirror, such that the mirror reflects the light onto the sample in a first light path, and the light is partly scattered at the sample and partly reflected at a plane or curved interface in the sample;
detecting scattered light from the sample by a detector situated in a second light path, and
directing a reference beam from the tunable light source onto the detector, the reference beam being off-axis to the second path; and configuring an angle of the mirror to reflect the light in the first light path, which is at an angle to the second light path; and wherein the mirror is not in the second light path;

wherein the tunable light source has a total coherence length, defined by the spectral width of the tuning range, not exceeding 50 μm, and an instantaneous coherence length, defined by the instantaneous line width of the spectral range during the scan, of at least 200 μm;

wherein the detector is configured to collect the reflected light from the sample via imaging the scattering volumetric sample or via the detection of wave fields from scatterers from all depths within the sample.

7. The method of claim 6, wherein the detector has an acquisition speed of at least 500 images per second.

8. An ophthalmologic imaging method comprising:

illuminating a sample by a beam from a tunable light source;

focusing the beam onto a hole of a mirror, such that the beam passes through the hole and illuminates a desired area in a sample through a lens, and the light is partly scattered at the desired area in the sample and partly reflected at a plane or curved interface in the sample, wherein the scattered light from the desired area in the sample is converted into far field light by a lens in the sample and the reflected light from the plane or curved interface in the sample is imaged back through the hole by the lens;

directing the far field light onto a detector by the mirror; and directing a reference beam from the tunable light source onto the detector, the reference beam being off-axis to a light path from the sample to the detector;

wherein the tunable light source has a total coherence length, defined by the spectral width of the tuning range, not exceeding 50 μm, and an instantaneous coherence length, defined by the instantaneous line width of the spectral range during the scan, of at least 200 μm;

wherein the detector is configured to collect the reflected light from the sample via imaging the scattering volumetric sample or via the detection of wave fields from scatterers from all depths within the sample.

9. The method of claim 8, wherein the sample is an eye and the desired area is on the retina of the eye, such that a focus is on or slightly beneath the cornea and the cornea reflex passes through the hole in the mirror, not reaching the detector.

10. The method of claim 8, wherein the detector has an acquisition speed of at least 500 images per second.

* * * * *